United States Patent [19]

Mazza

[11] 4,223,090

[45] Sep. 16, 1980

[54] REAGENTS FOR THE ENZYMATIC DETERMINATION OF TRIGLYCERIDES

[75] Inventor: John C. Mazza, Wenonah, N.J.

[73] Assignee: American Hospital Supply Corporation, Evanston, Ill.

[21] Appl. No.: 924,528

[22] Filed: Jul. 13, 1978

[51] Int. Cl.² .................................................. C12Q 1/44
[52] U.S. Cl. ........................................ 435/19; 435/25; 435/26; 435/190
[58] Field of Search .......... 195/62, 66 R, 99, 103.5 R; 435/18, 19, 25, 26, 190

[56] References Cited

U.S. PATENT DOCUMENTS

| | | | |
|---|---|---|---|
| 3,703,591 | 11/1972 | Bucolo et al. | 195/103.5 R |
| 4,038,146 | 7/1977 | Nonaka et al. | 195/103.5 R |
| 4,142,938 | 3/1979 | Stavropoulos et al. | 195/99 X |

OTHER PUBLICATIONS

Lin, et al, "The Activiation of Glycerol Dehydrogenase from *Aerobacter aerogenes* by Monovalent Cations", *J. Biol. Chem.*, vol. 235, No. 6, (1960), pp. 1820–1823.

*Primary Examiner*—Thomas G. Wiseman
*Attorney, Agent, or Firm*—E. A. Figg; R. E. Hartenberger

[57] ABSTRACT

A method of determining triglycerides in biological fluids according to an enzymatic reaction. In the reaction, a biological fluid is added to an enzyme reagent comprising a lipase, glycerol dehydrogenase (GDH), pyridine nucleotide (PN), a buffer, a tetrazolium compound and diaphorase, whereby the triglycerides are enzymatically hydrolyzed, and the resulting glycerol is oxidized to form a reduced pyridine nucleotide (PN) which reacts with said tetrazolium compound in the presence of the diaphorase to produce a colored formazan which is the reduced form of the tetrazolium, which color is measured at a wavelength ranging from about 475 to about 325 nm. The lipase is an enzyme obtained from *Chromobacterium viscosum*. In the enzyme reagent, there is from about 5.0 to about 15.0 I.U./ml of the glycerol dehydrogenase (GDH) present.

12 Claims, No Drawings

REAGENTS FOR THE ENZYMATIC DETERMINATION OF TRIGLYCERIDES

BACKGROUND OF THE INVENTION

The present invention related to a method of determining triglycerides in biological fluids according to an enzymatic reaction and a reagent for such method.

There has been a need for the determination of serum triglycerides ever since there has been evidence indicating a relationship between fat metabolism and such disorders as atherosclerosis, diabetes, hypertension, and increased risk of myocardial infarction.

The first direct procedure for the determination of triglycerides was published in 1957 by E. Van Handel and D. B. Zilversmit (J. Lab. and Clin. Med. (1957) 50, No. 1, p. 152). This procedure uses organic solvents to extract triglyerides from serum and solid phase adsorption to remove interferring phospholipids. Extracted triglycerides are saponified with KOH releasing glycerol. Glycerol is oxidized with periodate to formaldehyde. This is condensed with chromotropic acid to form a color complex. This basic procedure has been modified, but, in all the modifications, the chemistry and method of this system have remained essentially unchanged.

In 1966, M. Eggstein (Klin. Woochenschr 44, (1966), pp. 262-266) introduced a partially enzymatic method for determining serum triglycerides. In Eggstein's method the glycerol released from saponified triglyceride is phosphorylated by adenosine triphosphate (ATP) in the presence of an ATP-regenerating system sustained by phosphoenol-pyruvate degrading to pyruvate. A subsequent reduction of pyruvate to lactate by reduced nicotinamide adenine dinucleotide (i.e., NADH) is followed spectrophotometrically and is directly related to the glycerol concentration.

In 1973, G. Bucolo and H. David (Clin. Chem. 19 (1973), pp. 476-482) introduced a totally enzymatic procedure for the determination of serum triglycerides. In their method, alkaline saponification is replaced by an enzymatic hydrolysis:

Triglycerides 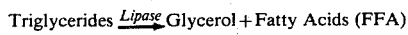 Glycerol + Fatty Acids (FFA)

The glycerol released by the enzymatic hydrolysis reacts according to the method presented by Eggstein. This method provided a clear improvement over the purely chemical and partial enzymatic methods, but it left much to be desired for the following reasons:

(a) the presence of internal blank rates;
(b) the instability of reconstituted reagents; and
(c) the necessity of rigid timing sequences.

There have been attempts to overcome the disadvantages of the method of Bocolo and David. These include an enzymatic reaction as described in French Pat. No. 2,314,497. In this French patent, enzymatic methods are described for the determination of glycerol which has been hydrolyzed from triglycerides by the reaction of a solution of Rhizopus Delemar lipase and alpha-chrymotrypsin. The glycerol involves the reduction of NAD by glycerol and utilizes either a single enzyme, glycerol dehydrogenase (GDH), or two enzymes, glycerol kinase (GK) and glycerol-3-phosphate dehydrogenase (GPDH). In both methods, the reaction yields reduce nicotinamide adenine dinucleotide (i.e., NADH) which quantity is proportional to that of glycerol.

The principal objective of the French invention is to provide a method of glycerol determination which allows for a quantitative assay in visible light.

Thus, there still remains a need for a dependable, specific enzymatic reaction to determine triglycerides in biological fluids. This need is satisfied as described below by the present invention.

SUMMARY OF THE INVENTION

The present method of determining triglycerides in biological fluids is carried out according to an enzymatic reaction. In the reaction, a biological fluid is added to an enzyme reagent comprising a lipase, glycerol dehydrogenase (GDH), pyridine nucleotide (PN), a buffer, a tetrazolium compound and diaphorase, whereby the triglycerides are enzymatically hydrolyzed, and the resulting glycerol is oxidized to form a reduced pyridine nucleotide (PN) which reacts with said tetrazolium compound in the presence of the diaphorase to produce a colored formazan, which color is measured at a wavelength ranging from about 475 to about 525 nm.

The lipase is an enzyme obtained from *Chromobacterium viscosum*. In the enzyme reagent, there is from about 5.0 to about 15.0 I.U./ml of the glycerol dehydrogenase (GDH) present.

DESCRIPTION OF PREFERRED EMBODIMENTS

The present invention employs a reagent containing enzymes, a tetrazolium compound and pyridine nucleotide (PN) for determining triglycerides in biological fluids.

According to the preferred embodiment, the method of determining the triglycerides is carried out according to an enzymatic reaction where a biological fluid is added and reacted with the enzymatic reagent.

The biological fluid may be any fluid which contains triglycerides such as serum.

The enzymatic reagent comprises a lipase, glycerol dehydrogenase (GDH), pyridine nucleotide (PN), a buffer, a tetrazolium compound and diaphorase.

In the reaction of the biological fluid and the enzymatic reagent, the triglycerides are enzymatically hydrolyzed and the resulting glycerol is oxidized to form a reduced pyridine nucleotide (PN) which reacts with the tetrazolium compound in the presence of diaphorase to produce a colored formazan. The color is measured at a wavelength ranging from about 475 to about 525 nm with the preferred wavelength being about 505 nm.

The overall enzymatic reaction sequence is as follows:

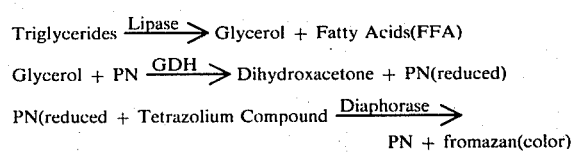

The function of the lipase in the enzyme reagent is to hydrolyze the triglycerides to fatty acids (FFA) and glycerol. The triglycerides, according to the present invention should be completely hydrolyzed.

The lipase may be selected from the following:
lipoprotein lipase (LPL)

Porcine pancreatic lipase
*Rhizopus arrhizus* lipase
*Candida cylindracea* lipase
Pseudomanas lipase The preferred lipase for hydrolyzing the triglycerides, however, is lipoprotein lipase (LPL) which is an enzyme obtained from *Chromobacterium viscosum.*

The amount of lipase present in the enzyme reagent ranges from about 100 to about 300 I.U./ml with the preferred amount being about 200 I.U./ml.

Glycerol dehydrogenase (GDH) is the most critical component of the enzymatic reagent. In the reaction, glycerol dehydrogenase (GDH) removes a hydrogen from glycerol and simultaneously converts the pyridine nucleotide (PN) to its reduced form.

Glycerol dehydrogenase (GDH) is an enzyme obtained from *Enterobacter aerogenes.* The amount of glycerol dehydrogenase (GDH) in the enzyme reagent may range from about 5.0 to about 15.0 I.U./ml with the preferred amount being about 10.0 I.U./ml.

The pyridine nucleotide which has provided the best results in the enzymatic reaction is nicotinamide adenine dinucleotide (NAD).

The nucleotide (NAD) oxidizes the glycerol produced by the hydrolysis of the triglycerides. The glycerol is oxidized by nicotinamide adenine dinucleotide (NAD) in the presence of glycerol dehydrogenase (GDH) to provide the reduced form of nicotinamide adenine dinucleotide (i.e., NADH) and dihydroxyacetone.

The reduced NAD formed (i.e., NADH) reacts with the tetrazolium compound in the presence of diaphorase to form a colored compound. Thus, in the enzymatic reaction, the nucleotide, i.e., NAD, is a necessary hydrogen carrier between glycerol and the tetrazolium compound.

The concentration of the nicotinamide adenine dinucleotide (NAD) in the enzyme reagent ranges from about 2.5 to about 5.5 mg/ml. The preferred concentration of NAD is 2.5 mg/ml.

The tetrazolium compound contained in the enzymatic reagent may be either iodophenyl nitrophenyl tetrazolium chloride (INT) or nitroblue tetrazolium chloride (NBT). The tetrazolium compounds have the following structural formulas:

Iodophenyl nitrophenyl tetrazolium chloride (INT)

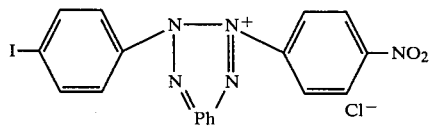

Nitroblue tetrazolium chloride (NBT)

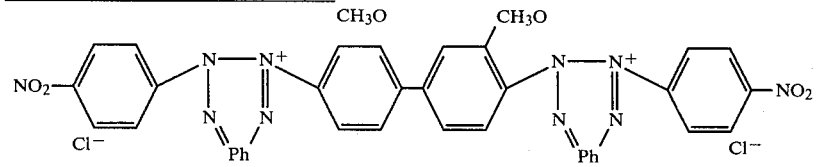

The tetrazolium compound is reduced to a red formazan when reacted with the reduced NAD (i.e., NADH). The red formazan absorbs light at a wavelength of about 505 nm.

The preferred tetrazolium compound is iodophenyl nitrophenyl tetrazolium chloride because it has a greater negative reduction potential. The concentration of the tetrazolium compound ranges from about 0.45 to about 1.35 mg/ml with the preferred concentration being about 0.90 mg/ml.

The enzyme diaphorase catalyzes the oxidation of the reduced nicotinamide adenine dinucleotide (NAD), i.e., NADH to NAD and thus, reduces the tetrazolium compound (i.e., INT) to a colored formazan.

The amount of diaphorase in the enzyme reagent may range from about 15.0 to about 45.0 I.U./ml with the preferred amount for optimal activity being about 28.5 I.U./ml.

Diaphorase is an enzyme obtained from *Clostridium kluyveri.*

The enzymes (i.e., lipase, GDH and diaphorase) of the enzyme reagent each have an individual pH optimum. The pH of the enzyme system must be such that all enzymes will function efficiently providing a reagent with good sensitivity. Thus, the pH of the reagent ranges from about 6.4 to about 8.0 with preferred pH being about 7.6

In the enzyme reagent, any suitable buffer may be used which is effective in the above-given pH range (i.e., 6.4 to 8.0). An effective buffer is potassium phosphate. Other buffers that may be used include triethonal-amine buffer, tris buffer, imidazole buffer and bicine buffer.

According to the invention, manganese is added to the glycerol dehyrogenase (GDH) to increase its reaction specificity. The manganese that may be added to the glycerol dehydogenase (GDH) will have a concentration ranging from about 0.05 to about 0.15 mM in the liquid substrate. The preferred concentration of manganese with the glycerol dehydrogenase is about 0.10 mM.

In the hydrolysis of the triglycerides, a diluent may be used such as solutions of Triton X-100, a surfactant (manufactured by Rohm and Haas Co., Philadelphia, Pennsylvania). Triton X-100 is an alkyl aryl polyether alcohol which is used to reduce the turbidity of the reaction. The Triton X-100 reduces the turbidity by solubilizing the fatty acids liberated during the lipase hydrolysis of the triglycerides.

The addition of as little as 0.5% volume (Triton X-100) to volume of water reduces blanks due to turbidity by as much as 1800%. However, the maximum amount of Triton X-100 is about 2.0% since the turbidity level measured at 660 nm is zero at the presence of 2% Triton X-100.

An acid such as HCl is included in the diluent with Triton X-100 to stop the reaction by denaturing the enzymes. The acid also serves to solubilize the formazan. It has been found that all acid concentrations stop the reaction and provide a stable final color. The concentration of HCl may range from 0.01 to about 0.20 mM. The preferred concentration of HCl is about 0.1 mM.

The following example further illustrates the present invention:

EXAMPLE

ENZYMATIC PROCEDURES FOR TRIGLYCERIDE DETERMINATION

In order to evaluate the effectiveness of the present enzymatic process, the characteristics and steps of the present method have been compared with those of other enzymatic procedures. The present method has been compared with the methods described in:

(A) Calbiochem, U.S. Pat. No. 3,703,591 issued Nov. 21, 1972;

(B) Boehringer Mannheim GMBH, U.S. Pat. No. 3,862,009 issued Jan. 21, 1975; and (C) Dow Chemical Co., U.S. Pat. No. 4,001,089 issued Jan. 4, 1977.

The characteristics and steps of the enzymatic procedures are recorded in the table below:

TABLE

ENZYMATIC PROCEDURES FOR TRIGLYCERIDE DETERMINATION

| Characteristics | Present Method | Calbiochem (A) |
|---|---|---|
| PRODUCT DESCRIPTION | Tri-ES | Triglycerides - Glycerol Reagent |
| TEST MEASURES | Endogenous glycerol | Endogenous glycerol |
| NUMBER OF TESTS | 95 | 50 |
| PRINCIPLE OF REACTION | $Tri \xrightarrow{Lipase} Gly + FFA$ | $Tri \xrightarrow{Lipase} Gly + FFA$ |
| | $Gly + NAD \xrightarrow{GDH}$ dihydroxyacetone + NADH | $Gly + ATP \xrightarrow{GK} \alpha GP + ADP$ |
| | | $ADP + PEP \xrightarrow{PK} ATP + Py$ |
| | $NADH + INT \xrightarrow{diaphorase}$ NAD + Formazan | $Py + NADH \xrightarrow{LDH} + Lac + NAD$ |
| SAMPLE SIZE | 20 µl | 50 µl |
| REAGENT PREPARATION | 1 - Reconstitute substrate | 3 - Reconstitute lipase add to reconstituted substrate vial. Reconstitute glycerol kinase. All prepared reagents 24 hrs @ 2–8° C. |
| RECONSTITUTED STABILTIY | Substrate 72 hrs @ 4° C. | |
| NO. OF REAGENTS | 2 + standard | 3 |
| PIPETTINGS | 3 | 3 |
| EXTRACTION | None | None |
| INCUBATION TIME/ TEMPERATURE | 1 for 20 min @ 37° C. | 3 for total of 33 min @ 30° C. |
| TIME/DETERMINATION | 25 min | 38 min |
| WAVELENGTH | 505 nm | 340 nm |
| LINEARITY | 700 mg/dl | 400 mg/dl |
| NORMAL RANGE | 50–167 mg/dl | Male 45 168 mg/dl; Female 49 170 |
| STANDARD PROVIDED | Yes | No |
| STORAGE | Refrigerate (2–8° C.) | Refrigerate (2–8° C.) |

| Characteristics | Boehringer Mannheim (B) | Dow Chemical (C) |
|---|---|---|
| PRODUCT DESCRIPTION | Triglycerides | Enzymatic Triglyceride |
| TEST MEASURES | Endogenous glycerol | Endogenous glycerol |
| NUMBER OF TESTS | 24 | 100 |
| PRINCIPLE OF REACTION | $Tri \xrightarrow{Lipase} Gly + FFA$ | $Tri \xrightarrow{Lipase} Gly + FFA$ |
| | $Gly + ATP \xrightarrow{GK} Gly\text{-}3\text{-}phos + ADP$ | $Gly + ATP \xrightarrow{Glycerol\ Kinase}$ gly 1 phs + ADP |
| | $ADP + PEP \xrightarrow{PK} ATP + Py$ | Gly 1 Phos + NAD |
| | $Py + NADH \xrightarrow{LDH} Lac + NAD$ | $\xrightarrow{gly\ 1\ phos\ dehydrogenase}$ dihydroxyacetone phos + |
| | | $NADH + INT \xrightarrow{Diaphorase}$ Formazan + NAD |
| SAMPLE SIZE | 50 µl | 20 µl |
| REAGENT PREPARATION | Reconstitute NADH solution. Combine solution 1,2, & 3 for test substrate | Reconstitute substrate |
| NO. OF REAGENTS | | 3 + standard |
| RECONSTITUTED STABILITY | Substrate 8 hrs @ R.T. or 30 hrs @ 4° C., NADH stable 2 weeks @ 4° C. | Substrate 24 hrs @ 4° C. |
| PIPETTINGS | 4 | 3 |
| EXTRACTIONS | 2 | None |
| INCUBATION TIME/ TEMPERATURE | None | 2 for total of 20 min @ 37° C. |
| TIME/DETERMINATION | 2 for total of 25 min @ R.T. or 15 min @ 37° C. | 25 min |
| FINAL COLOR STABILITY | 25 min | 10 min |

| TABLE-continued | | |
|---|---|---|
| ENZYMATIC PROCEDURES FOR TRIGLYCERIDE DETERMINATION | | |
| WAVELENGTH | 340 or 566 nm | 500 nm |
| LINEARITY | 580 mg/dl | 700 mg/dl |
| NORMAL RANGE | 72-172 mg/dl | 19-167 mg/dl |
| STANDARD PROVIDED | No | Yes |
| STORAGE | Refrigerate (2-8° C.) | Refrigerate (2-8° C.) |

From the information provided in the above table, it can readily be seen that the present invention is effective and has advantages over the previous enzymatic reactions for triglyceride determinations.

We claim:

1. In an enzyme reagent for detecting triglycerides in biological fluids which includes a lipase, glycerol dehydrogenase (GDH), pyridine nucleotide (PN), a buffer, a tetrazolium compound and diaphorase, the improvement which comprises manganese present at a concentration of from about 0.05 mM to about 0.15 mM.

2. The enzyme reagent of claim 1, wherein the lipase is present at a concentration of from about 100 to about 300 I.U./ml.

3. The enzyme reagent of claim 2, wherein the glycerol dehydrogenase (GDH) is present at a concentration of from about 5.0 to about 15.0 I.U./ml.

4. The enzyme reagent of claim 1, wherein the pyridine nucleotide (PN) is present at a concentration of from about 2.5 to about 7.5 mg/ml.

5. The enzyme reagent of claim 4, wherein the pyridine nucleotide (PN) is nicotinamide adenine dinucleotide (NAD).

6. The enzyme reagent of claim 1, wherein the diaphorase is present at a concentration of from about 15.0 to about 45.0 I.U./ml.

7. The enzyme reagent of claim 1, wherein the tetrazolium compound is present at a concentration of from about 0.45 to about 1.35 mg/ml.

8. The enzyme reagent of claim 7, wherein the tetrazolium compound is iodophenyl nitrophenyl tetrazolium chloride (INT).

9. The enzyme reagent of claim 1, wherein the pyridine nucleotide (PN), is nicotinamide adenine dinucleotide (NAD).

10. The enzyme reagent of claim 1, wherein the tetrazolium compound is iodophenyl nitrophenyl tetrazolium chloride (INT).

11. The enzyme reagent of claim 1, wherein the pH of the reagent is from about 6.4 to about 8.0.

12. The enzyme reagent of claim 1, wherein the lipase is a lipoprotein lipase obtained from a microorganism selected from the group consisting of *Chromobacterium viscosum, Enterobacter aerogenes,* and *Clostridium kluyveri,* and is present at a concentration of from about 100 to about 300 I.U./ml.; the glycerol dehydrogenase (GDH) is present at a concentration of from about 5.0 to about 15.0 I.U./ml.; the pyridine nucleotide (PN) is nicotinamide adenine dinucleotide (NAD), and is present at a concentration of from about 2.5 to about 7.5 mg/ml.; the diaphorase is present at a concentration of from about 15.0 to about 45.0 I.U./ml.; the tetrazolium compound is iodophenyl nitrophenyl tetrazolium chloride (INT) and is present at a concentration of from about 0.45 to about 1.35 mg/ml.; and the pH of the reagent is from about 6.4 to about 8.0.

* * * * *